United States Patent [19]
Palanki et al.

[11] Patent Number: 5,939,421
[45] Date of Patent: Aug. 17, 1999

[54] QUINAZOLINE ANALOGS AND RELATED COMPOUNDS AND METHODS FOR TREATING INFLAMMATORY CONDITIONS

[75] Inventors: Moorthy S. S. Palanki, Encinitas; Mark J. Suto, La Jolla, both of Calif.

[73] Assignee: Signal Pharmaceuticals, Inc., San Diego, Calif.

[21] Appl. No.: 08/886,198

[22] Filed: Jul. 1, 1997

[51] Int. Cl.$^6$ ........................ A01N 43/54; C07D 471/00; C07D 239/72
[52] U.S. Cl. ........................ 514/258; 514/259; 544/279; 544/293
[58] Field of Search ................................... 514/259, 258; 544/279, 293

[56] References Cited

U.S. PATENT DOCUMENTS 4,322,420  3/1982  Kobayashi et al. ..................... 424/251

FOREIGN PATENT DOCUMENTS

| 579 496 A1 | 1/1994 | European Pat. Off. . |
| WO 95/15758 | 6/1995 | WIPO . |
| WO 97/09315 | 3/1997 | WIPO . |
| WO 97/09325 | 3/1997 | WIPO . |

OTHER PUBLICATIONS

El–Sherief et al., "Quinazoline Derivatives from 2–Phenyl–4–quinazolinylhydrazine," *Bull. Chem. Soc. Jpn.* 57(4): 1138–1142, 1984.
El–Bahaie et. al., "Reactions with 4–Carboxymethylthio . . . ", Chem. Abs., vol. 116, ABS #151703W, p. 874, 1992.

*Primary Examiner*—Mukund J. Shah
*Assistant Examiner*—Tamthom N. Truong
*Attorney, Agent, or Firm*—Seed and Berry LLP

[57] ABSTRACT

Compounds having utility as anti-inflammatory agents in general and, more specifically, for the prevention and/or treatment of immunoinflammatory and autoimmune diseases are disclosed. The compounds are quinazoline-containing compounds. Methods are also disclosed for preventing and/or treating inflammatory conditions by administering to an animal in need thereof an effective amount of a compound of this invention, preferably in the form of a pharmaceutical composition.

25 Claims, 1 Drawing Sheet

QUINAZOLINE ANALOGS AND RELATED COMPOUNDS AND METHODS FOR TREATING INFLAMMATORY CONDITIONS

TECHNICAL FIELD

The present invention relates generally to compounds that block intracellular signal transduction and activation of transcription factors, and to methods for preventing or treating immunoinflammatory and autoimmune diseases.

BACKGROUND OF THE INVENTION

Signals necessary for cell growth, differentiation, response to bioregulatory molecules, infectious agents and physiological stress involve changes in the rates of gene expression. The ability to respond appropriately to such signaling events challenge the survival of the cell and ultimately the organism. Perturbations in the normal regulation of these specific genetic responses can result in pathogenic events which lead to acute and chronic disease.

In certain autoimmune diseases or chronic inflammatory states, continuous activation of T-cells eventually leads to a self-perpetuating destruction of normal tissues or organs. This is caused by the induction of adhesion molecules, chemotaxis of leukocytes, activation of leukocytes and the production of mediators of inflammation. All of these events are regulated at the level of transcription for the production of new proteins, including cytokines. The production of cytokines, as well as a number of other cellular regulators, is controlled by a family of proteins known as transcription factors (TFs). These transcription factors, when activated, bind to specific regions on the DNA and act as molecular switches or messengers to induce or upregulate gene expression. The activation of these TFs is caused by a variety of external signals including physiological stress, infectious agents and other bioregulatory molecules. Once the plasma membrane receptors are activated, a cascade of protein kinases and second messengers are induced which, in turn, result in the production of RNA transcripts. The end result is the production of proinflammatory proteins via translation and processing of the RNA transcripts.

This activation system can, at times, be very robust. For example, a specific set of external signals could result in a single transcription factor to induce many proteins responsible for a given disease. Therefore, regulating this process by disrupting the production of activated TF(s) has the potential to attenuate the production of the associated pathological proteins, thereby halting or reversing the course of the disease.

Two transcription factors, NFκB and AP-1, have been shown to regulate the production of many proinflammatory cytokines and related proteins that are elevated in immunoinflammatory diseases. These TFs regulate interleukin-1 (IL-1), interleukin-2 (IL-2), tumor necrosis factor-α (TNFα), interleukin-6 (IL-6) and interleukin-8 (IL-8) levels in a variety of cell types. For example, NFκB and other related complexes are involved in the rapid induction of genes whose products function in protective and proliferative responses upon exposure of cells to external stimuli. Similarly, AP-1 has a significant role in the regulation of interleukin-2 (IL-2) and tumor necrosis factor-α (TNF-α) transcription during T-cell activation. In addition, TNF-α and IL-1 are strong activators of collagenase, gelatinase and stromelysin gene expression, which require a single AP-1 binding site in the promoter region of these genes. Therefore, an inhibitor of NFκB and/or AP-1 activation would coordinately repress the activities of a series of proteinases. In addition, cell adhesion molecules are also controlled by these TFs. All of these proteins have been shown to play a role in diseases, including osteoarthritis, transplant rejection, ischemia, reperfusion injury, trauma, certain cancers and viral disorders, and autoimmune diseases such as rheumatoid arthritis, multiple sclerosis, psoriasis, inflammatory bowel disease, glomerulonephritis, lupus and juvenile diabetes. In summary, the role of these TFs is to act as a transducer for certain stimuli that lead to immune, inflammatory, and acute phase responses.

Since many diseases are caused by the inappropriate production of proteins, conventional therapeutic approaches have focused on inhibiting function or activity of individual effector proteins. These treatments have not always proved to be effective and, at times, are associated with many undesirable side effects. Therefore, there is a need for new therapies for the prevention and/or treatment of immunoinflammatory and autoimmune diseases. More specifically, there is a need for compounds that prevent, preferably by inhibiting transcription at an early stage, the production of proteins associated with immunoinflammatory and autoimmune diseases. Furthermore, these compounds should inhibit the kinase(s) that regulate the activation of TFs such as NFκB and AP-1. The present invention fulfills these needs and provides further related advantages.

SUMMARY OF THE INVENTION

In brief, this invention is directed to compounds that block the activation of transcription factors (TFs), particularly NFκB and AP-1, and are believed to function through inhibition of a family of specific kinases. This results in a decrease in a number of proinflammatory proteins, including IL-1, IL-2, IL-8 and/or TNFα, which are responsible for tissue and organ damage associated with diseases such as rheumatoid arthritis, osteoarthritis, related autoimmune disorders and tissue rejection. Accordingly, compounds of the present invention are useful in, for example, the prevention of organ and tissue rejection associated with transplantation. Furthermore, the compounds of this invention also have utility in the prevention and/or treatment of immunoinflammatory and autoimmune diseases, as well as having general activity as anti-inflammatory agents.

In one embodiment of this invention, compounds are disclosed having the following general structure (I):

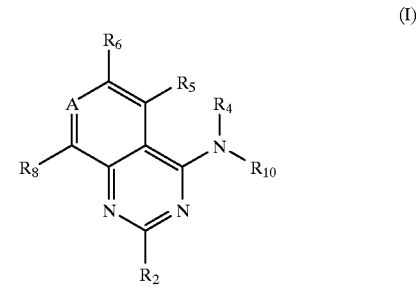

(I)

wherein A, $R_2$, $R_4$, $R_5$, $R_6$, $R_8$ and $R_{10}$ are as defined in the following detailed description.

In another embodiment, a pharmaceutical composition is disclosed containing one or more compounds of this invention in combination with a pharmaceutically or prophylactically acceptable carrier or diluent.

In a further embodiment, methods are disclosed for preventing and/or treating inflammatory conditions by administering to a warm-blooded animal in need thereof an effective amount of a compound of this invention. Such inflammatory conditions include both immunoinflammatory conditions and autoimmune diseases. In the practice of the disclosed methods, the compounds are preferably administered to the warm-blooded animal in the form of a pharmaceutical composition.

These and other aspects of this invention will become evident upon reference to the attached figures and the following detailed description.

DETAILED DESCRIPTION OF THE INVENTION

Figure 1:
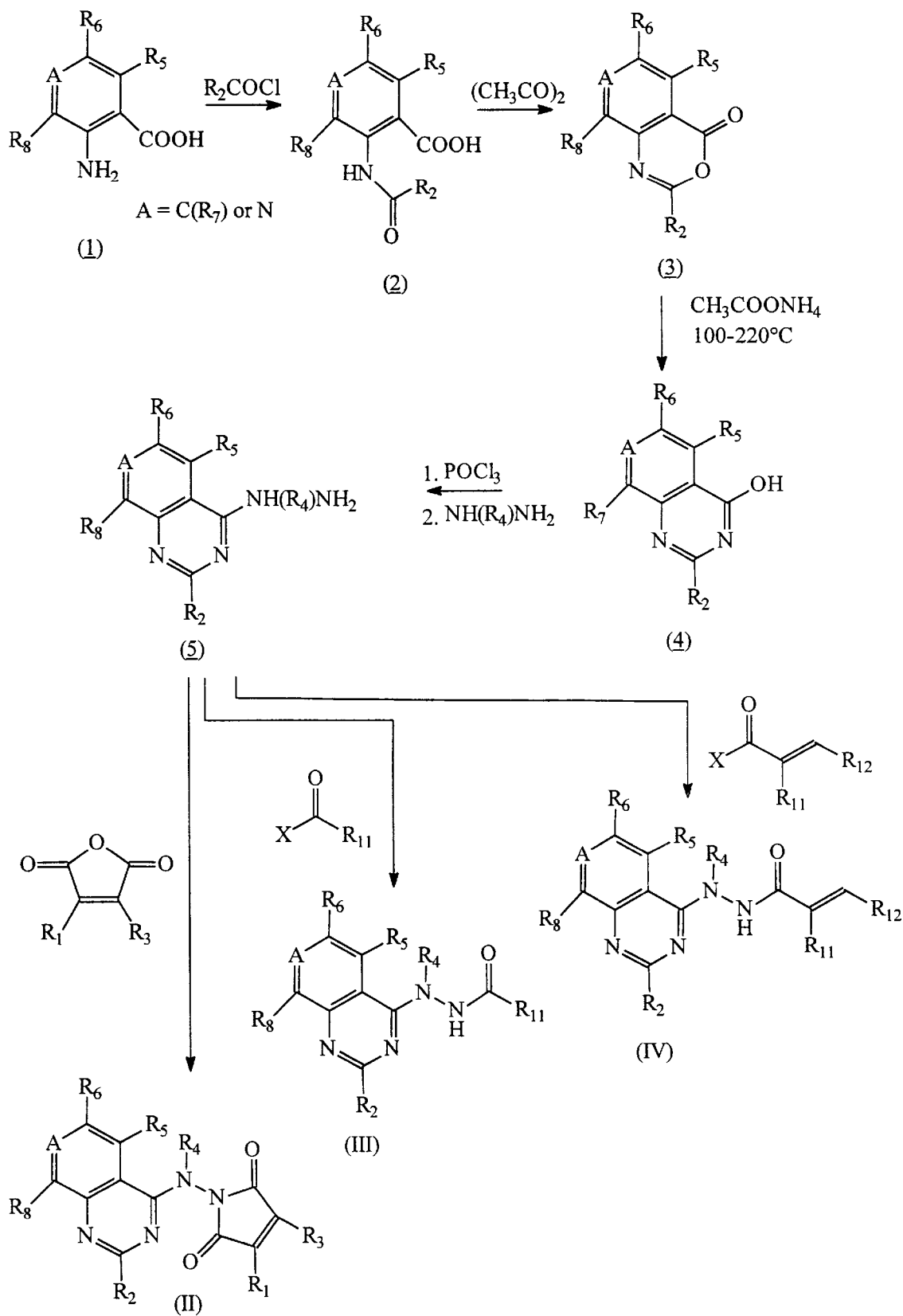
FIG. 1 illustrates a reaction scheme for the synthesis of representative quinazoline analogs of this invention.

The compounds of this invention block activation of transcription factors (TFs), and thus have utility as anti-inflammatory agents in general, and in the prevention and/or treatment of a variety of conditions, including (but not limited to) immunoinflammatory and autoimmune diseases. The compounds are believed to function by inhibiting, at an early stage, transcription of deleterious proteins associated with such conditions or diseases. It is believed that this is achieved by inhibiting the kinase(s) that regulate the activation of TFs, such as NFκB and/or AP-1. By disrupting the production of these activated TFs, synthesis of pathological proteins, including proinflammatory cytokines, associated with a series of immunoinflammatory and autoimmune diseases are effectively blocked at a transcriptional level. Accordingly, the compounds of this invention have activity in both the prevention and treatment of immunoinflammatory diseases such as rheumatoid arthritis, osteoarthritis and transplant rejection (tissue and organ), as well as autoimmune diseases such as multiple sclerosis.

As mentioned above, the compounds of this invention are generally represented by the following general structure (I):

(I)

wherein $R_{10}$ is selected from the following structures:

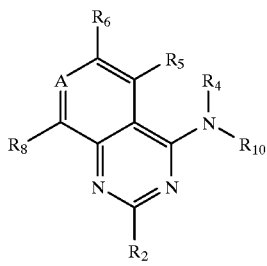

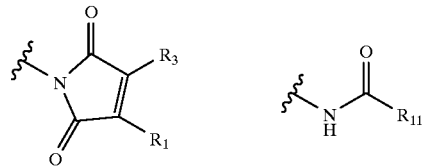

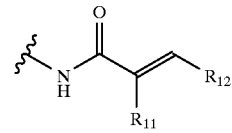

A is $C(R_7)$ or N;

$R_1$ and $R_3$ are independently selected from hydrogen or an unsubstituted or substituted $C_{1-8}$alkyl or $C_{6-12}$aryl;

$R_2$ is selected from an unsubstituted or substituted $C_{1-8}$alkyl, $C_{6-12}$aryl, $C_{7-12}$aralkyl, $C_{3-12}$heterocycle or $C_{4-16}$heterocyclealkyl;

$R_4$ is selected from hydrogen or an unsubstituted $C_{1-8}$alkyl;

$R_5$, $R_6$, $R_7$ and $R_8$ are independently selected from hydrogen, $-NO_2$, $-CN$, halogen, $C_{1-8}$alkyl, $X-C_{1-8}$alkyl, $C_{3-12}$heterocycle or $-COOR_9$, where X is selected from $-O-$, $-S-$, $-S(=O)-$, $-S(=O)_2-$, $-NH-$ or $-N(C_{1-8}$alkyl$)-$, and $R_9$ is selected from hydrogen or an unsubstituted or substituted $C_{1-8}$alkyl, $C_{6-12}$aryl or $C_{7-12}$aralkyl;

$R_{11}$ is selected from hydrogen or an unsubstituted or substituted $C_{1-8}$alkyl or $C_{6-12}$aryl; and $R_{12}$ is selected from hydrogen; $-COOR_9$, $-CONHR_9$, or an unsubstituted or substituted $C_{1-8}$alkyl or $C_{6-12}$aryl.

As used herein, the above terms have the following meaning:

A "$C_{1-8}$alkyl" is a straight chain or branched, cyclic or non-cyclic, saturated or unsaturated carbon chain containing from 1 to 8 carbon atoms. In one embodiment, the $C_{1-8}$alkyl is a fully saturated, straight chain alkyl selected from methyl, ethyl, n-propyl, n-butyl, n-pentyl and n-hexyl. In another embodiment, the $C_{1-8}$alkyl is a fully saturated cyclic alkyl selected from (but not limited to) cyclopropyl, cyclobutyl, cyclopentyl, cyclohexyl, methylenecyclopropyl and methylenecyclohexyl. In still a further embodiment, the $C_{1-8}$alkyl is a fully saturated, branched alkyl selected from (but not limited to) isopropyl, sec-butyl, isobutyl, tert-butyl, isopentyl and isohexyl. In yet a further embodiment, the $C_{1-8}$alkyl is an unsaturated straight chain alkyl selected from (but not limited to) ethylenyl, propylenyl, 1-butenyl, 1-pentenyl and 1-hexenyl.

A "$C_{6-12}$aryl" is an aromatic moiety containing from 6 to 12 carbon atoms. In one embodiment, the $C_{6-12}$aryl is selected from (but not limited to) phenyl, tetralinyl, and napthalenyl. In a preferred embodiment, the $C_{6-12}$aryl is phenyl.

A "$C_{7-12}$aralkyl" is an arene containing from 7 to 12 carbon atoms, and has both aliphatic and aromatic units. In one embodiment, the $C_{7-12}$aralkyl is selected from (but not limited to) benzyl, ethylbenzyl, propylbenzyl and isobutylbenzyl.

A "$C_{3-12}$heterocycle" is a compound that contains a ring made up of more than one kind of atom, and which contains 3 to 12 carbon atoms. In one embodiment, the $C_{3-12}$heterocycle is selected from (but not limited to) pyrrolyl, furanyl, thiophenyl, imidazolyl, oxazolyl, thiazolyl, pyrazolyl, pyrrolidinyl, pyridinyl, pyrimidinyl and purinyl.

A "$C_{4-16}$heterocyclealkyl" is a compound that contains a $C_{3-12}$heterocycle linked to a $C_{1-8}$alkyl. In one embodiment, the $C_{4-16}$heterocyclealkyl is a methylene furan having the following structure:

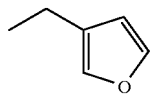

A "substituted" $C_{1-8}$alkyl, $C_{6-12}$aryl, $C_{7-12}$arakyl, $C_{3-12}$heterocycle or $C_{4-16}$heterocyclealkyl is a $C_{1-8}$alkyl, $C_{6-12}$aryl, $C_{7-12}$aralkyl, $C_{3-12}$heterocycle or $C_{4-16}$heterocyclealkyl having one or more hydrogens replaced with a substituent selected from halogen (including —F, —Cl, —Br and —I), —OH, —R, —OR, —COOH, —COOR, —COR, —CONH$_2$, —NH$_2$, —NHR, —NRR, —SH, —SR, —SOOR, —SOOH and —SOR, where each occurrence of R is independently selected from an unsubstituted or substituted $C_{1-8}$alkyl, $C_{6-12}$aryl, $C_{7-12}$aralkyl, $C_{3-12}$heterocycle or $C_{4-16}$heterocyclealkyl as defined above. In one embodiment, the substituted $C_{1-8}$alkyl is a $C_{1-8}$haloalkyl including (but not limited to) —CF$_3$ and —C$_2$F$_5$.

Accordingly, depending upon the $R_{10}$ moiety, the compounds of this invention have the following structures (II), (III) or (IV):

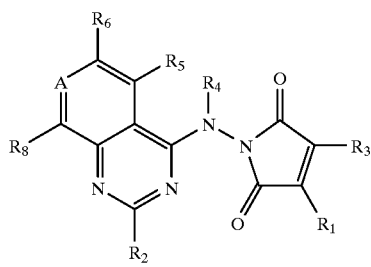

(II)

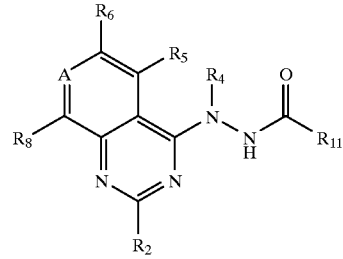

(III)

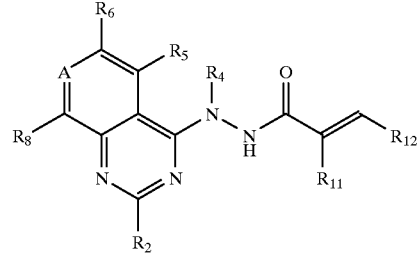

(IV)

where A, $R_1$, $R_2$, $R_3$, $R_4$, $R_5$, $R_6$, $R_8$, $R_{11}$ and $R_{12}$ are as defined above. (In Structure (IV) above, the $R_{12}$ moiety may be in the cis- or trans- configuration.)

Representative compounds of this invention having structure (II) above are set forth in Table 1, while compounds having structure (IV) above are set forth in Table 2.

TABLE 1

Representative Compounds of Structure (II)

| Cp.No. | $R_1$ | $R_2$ | $R_3$ | $R_4$ | $R_5$ | $R_6$ | $R_7$ | $R_8$ | A |
|---|---|---|---|---|---|---|---|---|---|
| 1 | CH$_3$ | C$_6$H$_5$ | H | H | H | H | H | H | C(R$_7$) |
| 2 | CH$_3$ | 2'-thienyl | H | H | H | H | — | H | N |
| 3 | CH$_3$ | CF$_3$ | H | H | H | H | H | H | C(R$_7$) |
| 4 | CH$_3$ | CF$_3$ | H | H | OCH$_3$ | H | H | H | C(R$_7$) |
| 5 | CH$_3$ | CF$_3$ | H | H | CH$_3$ | H | H | H | C(R$_7$) |
| 6 | CH$_3$ | CF$_3$ | H | H | H | H | Cl | H | C(R$_7$) |
| 7 | CH$_3$ | CF$_3$ | H | H | H | H | piperioyl | H | C(R$_7$) |
| 8 | CH$_3$ | CF$_3$ | H | H | H | SCH$_3$ | H | .H | C(R$_7$) |
| 9 | CH$_3$ | CF$_3$ | H | H | H | S(O)CH$_3$ | H | H | C(R$_7$) |
| 10 | CH$_3$ | CF$_3$ | H | H | H | S(O)$_2$CH$_3$ | H | H | C(R$_7$) |
| 11 | CH$_3$ | 2'-thienyl | H | H | H | H | H | H | C(R$_7$) |
| 12 | CH$_3$ | 2'-thienyl | H | CH$_3$ | H | H | H | H | C(R$_7$) |
| 13 | CH$_3$ | 2'-thienyl | H | H | OCH$_3$ | H | H | H | C(R$_7$) |
| 14 | CH$_3$ | 2'-thienyl | H | H | H | OCH$_3$ | H | H | C(R$_7$) |
| 15 | CH$_3$ | 2'-thienyl | H | H | H | H | OCH$_3$ | H | C(R$_7$) |
| 16 | CH$_3$ | 2'-thienyl | H | H | H | H | H | OCH$_3$ | C(R$_7$) |
| 17 | CH$_3$ | 2'-thienyl | H | H | H | OCH$_3$ | OCH$_3$ | H | C(R$_7$) |
| 18 | CH$_3$ | 2'-thienyl | H | H | H | OCH$_3$ | OCH$_3$ | OCH$_3$ | C(R$_7$) |
| 19 | CH$_3$ | 2'-thienyl | H | CH$_3$ | OCH$_3$ | H | H | H | C(R$_7$) |
| 20 | CH$_3$ | 2'-thienyl | H | H | F | H | H | H | C(R$_7$) |
| 21 | CH$_3$ | 2'-thienyl | H | H | Cl | H | H | H | C(R$_7$) |
| 22 | CH$_3$ | 2'-thienyl | H | H | CH$_3$ | H | H | H | C(R$_7$) |
| 23 | CH$_3$ | 2'-thienyl | H | H | H | H | N(CH$_3$)2 | H | C(R$_7$) |

TABLE 2

Representative Compounds of Structure (IV)

| Cp.No. | R$_2$ | R$_4$ | R$_5$ | R$_6$ | R$_7$ | R$_8$ | R$_{11}$ | R$_{12}$ | A |
|---|---|---|---|---|---|---|---|---|---|
| 24 | CF$_3$ | H | H | H | H | H | CH$_3$ | COOH | C(R$_7$) |
| 25 | 2'-thienyl | H | H | OCH$_3$ | H | H | CH$_3$ | COOH | C(R$_7$) |

The compounds of this invention may be made by one skilled in organic synthesis by known techniques, as well as by the synthetic routes disclosed herein. For example, the quinazoline analogs of structure (II) above may be prepared according to the following reaction scheme set for in FIG. 1. In brief, commercially available —COOH and —NH$_2$ substituted phenyl (A=C(R$_7$)) or pyridine (A=N) compounds (1) are treated with an acid chloride to yield amide (2), which is then cyclized by acetic anhydride to form lactone (3). The lactone is converted to lactam (4) with ammonium acetate under elevated heat and pressure, followed by conversion of the lactam to hydrazine derivative (5). Lastly, the hydrazine derivative is reacted with an appropriately substituted cyclic anhydride to yield structure (II). The synthesis of compounds having structures (III) and (IV) may be similarly made from hydrazine derivative (5) by addition of an appropriately activated carboxylic acid or activated α, β-unsaturated acid, respectively. The synthesis of representative compounds of this invention are further disclosed in Examples 1–81.

Once synthesized, the compounds of this invention may be formulated for administration to a warm-blooded animal by a variety of techniques known to those skilled in the art. In one embodiment, the compound is in the form of a pharmaceutical composition for prophylactic or therapeutic use, and which contains at least one compound of this invention in combination with a pharmaceutically acceptable carrier or diluent. The compound is present in the composition in an amount which, upon administration to the animal, is effective in preventing or treating the condition of interest. Preferably, the composition includes a compound of this invention in an amount ranging from 0.01 mg to 250 mg per dosage, depending upon the route of administration, and more preferably from 1 mg to 60 mg. Appropriate concentrations, dosages and modes of administration may be readily determined by one skilled in the art.

Suitable carriers or diluents are familiar to those skilled in the formulation field. For compositions formulated as liquid solutions, acceptable carrier or diluents include saline and sterile water, and may optionally include antioxidants, buffers, bacteriostats and other common additives. The compositions of this invention may also be formulated as pills, capsules, granules or tablets which contain, in addition to the compound of this invention, diluents, dispersing and surface active agents, binders and lubricants. One skilled in the art may further formulate the compounds of this invention in any appropriate manner, and in accordance with accepted practices, such as those disclosed in *Remington's Pharmaceutical Sciences*, Gennaro, Ed., Mack Publishing Co., Easton, Pa., 1990 (incorporated herein by reference).

In another embodiment, the present invention provides methods for preventing or treating a variety of conditions. Such methods include administering a compound of this invention to a warm-blooded animal in need thereof in an amount sufficient to prevent or treat the condition. Such methods include systemic administration of a compound of this invention, preferably in the form of a composition as disclosed above. As used herein, systemic administration includes oral and parental methods of administration. For oral administration, suitable pharmaceutical compositions include powders, granules, pills, tablets and capsules, as well as liquids, syrups, suspensions and emulsions. These compositions may also include flavorants, preservatives, suspending, thickening and emulsifying agents, and other pharmaceutically acceptable additives. For parental administration, the compounds of the present invention may be prepared in aqueous injectable solutions which may contain, in addition to the compound of this invention, buffers, antioxidants, bacteriostats and other additives commonly employed in such solutions.

As mentioned above, compounds of the present invention can be used to prevent or treat a wide variety of disorders, diseases and/or illnesses. In particular, the compounds may be administered to a warm-blooded animal for prevention or treatment of rheumatoid arthritis, osteoarthritis, tissue and/or organ transplant rejection, sepsis, ARDS, asthma, trauma, oxidative stress, cell death, irradiation damage, ischemia, reperfusion, cancer, viral infection, and autoimmune diseases such as psoriasis, inflammatory bowel disease, glomerulonephritis, lupus, uveitis and chronic hepatitis.

Compounds of this invention may be screened by known and accepted techniques for their ability to finction as prophylactically and/or therapeutically active agents. For example, the compounds may be evaluated in in vitro and/or in vivo assays indicative of the compound's anti-inflammatory and immunosuppressive properties. To this end, such compounds may first be evaluated in a number of cell-based assays which determine the ability of a compound to prevent activation of NFκB and AP-1 (see Example 79). Next, the compound's ability to attenuate cytokine levels (such as IL-2 and IL-8), which are known to be elevated in certain disease states, may be determined (see Example 80). The compounds may then be evaluated in an appropriate animal model, including rodent models of inflammation and immunosuppression.

The following examples are presented for purpose of illustration, not limitation.

EXAMPLES

To summarize the examples that follow, Examples 1–81 disclose the synthesis of representative compounds of this invention, as well as intermediates thereof; Examples 82–83 disclose the ability of representative compounds of this invention to inhibit NFκB, AP-1 and cytokines; and Example 84 discloses in vivo assays for evaluating activity of the compounds of this invention.

Example 1

2-(2'-THIENYL)-4H-3,1-BENZOXAZIN-4-ONE

A solution of anthranilic acid (2.0 g, 15 mmol), 2-thienylcarbonyl chloride (2.2 g, 15 mmol), and triethylamine (1.5 g, 15 mmol) in ethyl acetate (9 mL) was stirred for 1 h. The solution was filtered and concentrated to a solid (3.7 g, 99%). The solid (1 g, 4 mmol) was heated at reflux with acetic anhydride (20 mL) for 18 h. The reaction mixture was concentrated, washed with water, and dried to give the title compound (0.92 g, 99%); m.p. 129–130° C.

Example 2

4-HYDROXY-2-(2'-THIENYL)QUINAZOLINE

A mixture of 2-(2'-thienyl)-4H-3,1-benzoxazin-4-one (0.22 g, 0.94 mmol) and ammonium acetate (0.15 g, 1.9 mmol) was heated at 220° C. for 3 h. The reaction mixture was cooled to room temperature and the solid was washed with water and dried to give the title compound (0.21 g, 97%); m.p. 274–275° C.

Example 3

4-CHLORO-2-(2'-THIENYL)QUINAZOLINE

A mixture of 4-hydroxy-2-(2'-thienyl)quinazoline (0.4 g, 1.8 mmol) and phosphorus oxychloride (1.3 g, 8.8 mmol) was heated at 115° C. for 0.25 h. The reaction mixture was poured on to ice and extracted with ethyl acetate. The ethyl acetate layer was dried ($Na_2SO_4$), filtered and concentrated to give the title compound (0.41 g, 95%);

m.p. 210–211° C.

Example 4

4-(N-AMINOCITRACONAMIDO)-2-(2'-THIENYL) QUNINAZOLINE

A solution of 4-chloro-2-(2'-thienyl)quinazoline (0.19 g, 0.75 mmol), and hydrazine in THF (7.5 mL) was stirred for 0.25 h. The solution was filtered through a silica plug and eluted with ethyl acetate. The filtrate was concentrated to a solid. The solid, and citraconic anhydride (0.24 g, 2.1 mmol) was dissolved in chloroform (7 mL), and heated at reflux for 18 h. The solution was concentrated and chromatographed ($SiO_2$, 33% ethyl acetate in hexanes) to give the title compound (0.15 g, 98%); m.p. 100–101° C.

Example 5

4-(N-METHYL-N-AMINOCITRACONAMIDO)-2-(2'-THIENYL)QUNINAZOLINE

A solution of 4-chloro-2-(2'-thienyl)quinazoline (0.2 g, 0.83 mmol), and N-methylhydrazine (0.19 g, 4.1 mmol) in THF (8 mL) was stirred at room temperature for 0.5 h. The solution was filtered through a silica plug and eluted with ethyl acetate. The filtrate was concentrated to a solid. The solid, and citraconic anhydride (0.26 g, 2.3 mmol) were dissolved in chloroform (16 mL) and heated at reflux for 18 h. The reaction mixture was concentrated and crystallized from 25% ether-hexane to give the title compound (0.18 g, 99%); m.p. 140–141° C.

Example 6

5-METHOXY-2-(2'-THIENYL)-4H-3,1-BENZOXAZIN-4-ONE

The title compound was prepared from 2-amino-6-methoxybenzoic acid (4.5 g, 27 mmol) as described in Example 1, to provide the desired compound in a 36% (2.5 g) yield; m.p. 117–119° C.

Example 7

4-HYDROXY-5-METHOXY-2-(2'-THIENYL) QUINAZOLINE

The title compound was prepared from 5-methoxy-2-(2'-thienyl)-4H-3,1-benzoxazin-4-one (1 g, 3.9 mmol) as described in Example 2 to provide the desired compound in a 80% (0.8 g) yield; m.p. 268–270° C.

Example 8

4-CHLORO-5-METHOXY-2-(2'-THIENYL) QUINAZOLINE

The title compound was prepared from 4-hydroxy-5-methoxy-2-(2'-thienyl)quinazoline (1.2 g, 4.7 mmol) as described in Example 3 to provide the desired compound in a 65% (0.84 g) yield; m.p. 98–99° C.

Example 9

4-(N-AMINOCITRACONAMIDO)-5-METHOXY-2-(2'-THIENYL)QUINAZOLINE

The title compound was prepared from 4-chloro-5-methoxy-2-(2'-thienyl)quinazoline (0.84 g, 3 mmol) as described in Example 4 to provide the desired compound in a 83% (0.91 g) yield; m.p. 199–200° C.

Example 10

4-(N-METHYL-N-AMINOCITRACONAMIDO)-5-METHOXY-2-(2'-THIENYL)QUNINAZOLINE

The title compound was prepared from 4-chloro-5-methoxy-2-(2'-thienyl)quinazoline (0.12 g, 0.42 mmol) as described in Example 5 to provide the desired compound in a 22% (0.03 g) yield; m.p. 88–89° C.

Example 11

6-METHOXY-2-(2'-THIENYL)-4H-3,1-BENZOXAZIN-4-ONE

The title compound was prepared from 2-amino-5-methoxybenzoic acid (2.0 g, 12 mmol), as described in Example 1 to provide the desired compound in a 47% (1.4 g) yield; m.p. 135–137° C.

Example 12

4-HYDROXY-6-METHOXY-2-(2'-THIENYL) QUNINAZOLINE

The title compound was prepared from 6-methoxy-2-(2'-thienyl)-4H-3,1-benzoxazin-4-one (1.3 g, 5.0 mmol) as described in Example 2 to provide the desired compound in a 85% (1.1 g) yield; m.p. 208–210° C.

Example 13

4-CHLORO-6-METHOXY-2-(2'-THIENYL)QUINAZOLINE

The title compound was prepared from 4-hydroxy-6-methoxy-2-(2'-thienyl)quinazoline (1.1 g, 4.3 mmol) as described in Example 3 to provide the desired compound in a 38% (0.45 g) yield; m.p. 123–125° C.

Example 14

4-(N-AMINOCITRACONAMIDO)-6-METHOXY-2-(2'-THIENYL)QUINAZOLINE

The title compound was prepared from 4-chloro-6-methoxy-2-(2'-thienyl)quinazoline (0.35 g, 1.3 mmol) as described in Example 4 to provide the desired compound in a 45% (0.12 g) yield; m.p. 245–247° C.

Example 15

7-METHOXY-2-(2'-THIENYL)-4H-3,1-BENZOXAZIN-4-ONE

The title compound was prepared from 2-amino-4-methoxybenzoic acid (1.5 g, 9 mmol) as described in Example 1 to provide the desired compound in a 87% (1.6 g) yield; m.p. 129–130° C.

Example 16

4-HYDROXY-7-METHOXY-2-(2'-THIENYL) QUNINAZOLINE

The title compound was prepared from 7-methoxy-2-(2'-thienyl)-4H-3,1-benzoxazin-4-one (1.7 g, 6.6 mnmol) as described in Example 2 to provide the desired compound in a 91% (1.6 g) yield; m.p. 240–241° C.

Example 17

4-CHLORO-7-METHOXY-2-(2'-THIENYL) QUNINAZOLINE

The title compound was prepared from 4-hydroxy-7-methoxy-2-(2'-thienyl)quinazoline (0.33 g, 1.3 mmol) as described in Example 3 to provide the desired compound in a 79% (0.28 g) yield; m.p. 100–101° C.

Example 18

4-(N-AMINOCITRACONAMIDO)-7-METHOXY-2-(2'-THIENYL)QUINAZOLINE

The title compound was prepared from 4-chloro-7-methoxy-2-(2'-thienyl)quinazoline (0.27 g, 0.98 mmol) as described in Example 4 to provide the desired compound in a 83% (0.28 g,) yield; m.p. 191–192° C.

Example 19

8-METHOXY-2-(2'-THIENYL)-4H-3,1-BENZOXAZIN-4-ONE

The title compound was prepared from 2-amino-3-methoxybenzoic acid (4 g, 24 mmol) as described in Example 1 to provide the desired compound in a 91% (5.1 g) yield; m.p. 135–136° C.

Example 20

4-HYDROXY-8-METHOXY-2-(2'-THIENYL) QUNINAZOLINE

The title compound was prepared from 8-methoxy-2-(2'-thienyl)-4H-3,1-benzoxazin-4-one (2 g, 7.7 mmol) as described in Example 2 to provide the desired compound in a 85% (1.7 g) yield; m.p. 261–262° C.

Example 21

4-CHLORO-8-METHOXY-2-(2'-THIENYL) QUNINAZOLINE

The title compound was prepared from 4-hydroxy-8-methoxy-2-(2'-thienyl)quinazoline (0.33 g, 1.3 mmol) as described in Example 3 to provide the desired compound in a 80% (0.29 g) yield; m.p. 112–113° C.

Example 22

4-(N-AMINOCITRACONAMIDO)-8-METHOXY-2-(2'-THIENYL)QUNINAZOLINE

The title compound was prepared from 4-chloro-8-methoxy-2-(2'-thienyl)quinazoline (0.29 g, 1.04 mmol) as described in Example 4 to provide the desired compound in a 83% (0.29 g) yield; m.p. 206–207° C.

Example 23

6,7-DIMETHOXY-2-(2'-THIENYL)-4H-3,1-BENZOXAZIN-4-ONE

The title compound was prepared from 2-amino-4,5-dimethoxybenzoic acid (7 g, 36 mmol) as described in Example 1 to provide the desired compound in a 49% (5 g) yield; m.p. 209–210° C.

Example 24

4-HYDROXY-6,7-DIMETHOXY-2-(2'-THIENYL) QUINAZOLINE

The title compound was prepared from 6,7-dimethoxy-2-(2'-thienyl)-4H-3,1-benzoxazin-4-one (3.0 g, 10 mmol) as described in Example 2 to provide the desired compound in a 63% (1.9 g) yield; m.p. 252–255° C.

Example 25

4-CHLORO-6,7-DIMETHOXY-2-(2'-THIENYL) QUNINAZOLINE

The title compound was prepared from 4-hydroxy-6,7-dimethoxy-2-(2'-thienyl)quinazoline (1.7 g, 5.9 mmol) as described in Example 3 to provide the desired compound in a 38% (0.7 g) yield; m.p. 168–170° C.

Example 26

4-(N-AMINOCITRACONAMIDO)-6,7-DIMETHOXY-2-(2'-THIENYL)QUINAZOLINE

The title compound was prepared from 4-chloro-6,7-dimethoxy-2-(2'-thienyl)quinazoline (0.3 g, 0.98 mmol) as described in Example 4 to provide the desired compound in a 64% (0.1 g) yield; m.p. 74–75° C.

Example 27

6,7,8-TRIMETHOXY-2-(2'-THIENYL)-4H-3,1-BENZOXAZIN-4-ONE

The title compound was prepared from 2-amino-3,4,5-trimethoxybenzoic acid (3.0 g, 13 mmol) as described in Example 1 to provide the desired compound in a 5 89% (2.5 g) yield; m.p. 146–147° C.

Example 28

4-HYDROXY-6,7,8-TRIMETHOXY-2-(2'-THIENYL) QUNINAZOLINE

The title compound was prepared from 6,7,8-trimethoxy-2-(2'-thienyl)-4H-3,1-benzoxazin-4-one (1.5 g, 4.7 mmol) as described in Example 2 to provide the desired compound in a 80% (1.2 g) yield; m.p. 195–196° C.

Example 29

4-CHLORO-6,7,8-TRIMETHOXY-2-(2'-THIENYL) QUINAZOLINE

The title compound was prepared from 4-hydroxy-6,7,8-trimethoxy-2-(2'-thienyl)quinazoline (0.23 g, 0.72 mmol) as described in Example 3 to provide the desired compound in a 69% (0.17 g) yield; GC/MS calcd for $C_{15}H_{13}ClN_2O_3S$ (M+) 336, found 336.

Example 30

4-(N-AMINOCITRACONAMIDO)-6,7,8-TRIMETHOXY-2-(2'-THIENYL)QUNINAZOLINE

The title compound was prepared from 4-chloro-6,7,8-trimethoxy-2-(2'-thienyl)quinazoline (0.17 g, 0.5 mmol) as described in Example 4 to provide the desired compound in a 35% (0.06 g) yield; m.p. 115–116° C.

Example 31

4-HYDROXY-5-FLUORO-2-(2'-THIENYL) QUNINAZOLINE

The title compound was prepared from 5-fluoro-2-(2'-thienyl)-4H-3,1-benzoxazin-4-one (0.98 g, 4.0 mmol) as described in Example 2 to provide the desired compound in a 92% (0.9 g) yield; m.p. 291–294° C.

Example 32

4-Chloro-5-Fluoro-2-(2'-Thienyl)Quinazoline

The title compound was prepared from 4-hydroxy-5-fluoro-2-(2'-thienyl)quinazoline (0.9 g, 3.7 mmol) as described in Example 3 to provide the desired compound in a 85% (0.9 g) yield; m.p. 160–162° C.

Example 33

4-(N-Aminocitraconamido)-5-Fluoro-2-(2'-Thienyl)Quinazoline

The title compound was prepared from 4-chloro-5-fluoro-2-(2'-thienyl)quinazoline (0.88 g, 3.3 mmol) as described in Example 4 to provide the desired compound in a 63% (0.3 1 g) yield; m.p. 214–215° C.

Example 34

4-Hydroxy-5-Chloro-2-(2'-Thienyl)Quinazoline

The title compound was prepared from 5-chloro-2-(2'-thienyl)-4H-3,1-benzoxazin-4-one (1.0 g, 3.8 mmol), as described in Example 2 to provide the desired compound in a 70% (0.7 g) yield; m.p. 249–252° C.

Example 35

4,5-Dichloro-2-(2'-Thienyl)Quninazoline

The title compound was prepared from 4-hydroxy-5-chloro-2-(2'-thienyl)quinazoline (0.5 g, 1.9 mmol) as described in Example 3 to provide the desired compound in a 95% (0.51 g) yield; m.p. 134–135° C.

Example 36

4-(N-Aminocitraconamido)-5-Chloro-2-(2'-Thienyl)Quinazoline

The title compound was prepared from 4,5-dichloro-2-(2'-thienyl)quinazoline (0.5 g, 1.8 mmol), as described in Example 4 to provide the desired compound in a 8% (0.05 g) yield; m.p. 205–206° C.

Example 37

5-Methyl-2-(2'-Thienyl)-4H-3, 1-Benzoxazin-4-One

The title compound was prepared from 2-amino-6-methylbenzoic acid (5 g, 33 mmol) as described in Example 1 to provide the desired compound in a 63% (5 g) yield; m.p. 127–128° C.

Example 38

4-Hydroxy-5-Methyl-2-(2'-Thienyl)Quinazoline

The title compound was prepared from 5-methyl-2-(2'-thienyl)-4H-3,1-benzoxazin-4-one (2.0 g, 8 mmol) as described in Example 2 to provide the desired compound in a 84% (1.6 g) yield; m.p. 280–283° C.

Example 39

4-Chloro-5-Methyl-2-(2'-Thienyl)Quninazoline

The title compound was prepared from 4-hydroxy-5-methyl-2-(2'-thienyl)quinazoline (1.0 g, 4.1 mmol) as described in Example 3 to provide the desired compound in a 50% (0.53 g) yield; m.p. 121–123° C.

Example 40

4-(N-Aminocitraconamido)-5-Methyl-2-(2'-Thienyl)Quninazoline

The title compound was prepared from 4-chloro-5-methyl-2-(2'-thienyl)quinazoline (0.3 g, 1.1 mmol) as described in Example 4 to provide the desired compound in a 20% (0.06 g) yield; m.p. 94–95° C.

Example 41

7-Chloro-2-(2'-Thienyl)-4H-3,1-Benzoxazin-4-One

The title compound was prepared from 2-amino-4-chlorobenzoic acid (20 g, 116 mmol) as described in Example 1 to provide the desired compound in a 58% (18 g) yield; m.p. 158–160° C.

Example 42

7-Chloro-4-Hydroxy-2-(2'-Thienyl)Quinazoline

The title compound was prepared from 7-chloro-2-(2'-thienyl)-4H-3,1-benzoxazin-4-one (11 g, 43 mmol) as described in Example 2 to provide the desired compound in a 89% (10 g) yield; m.p. 204–205° C.

Example 43

7-Dimethylamino-4-Hydroxy-2-(2'-thienyl)Quninazoline

A solution of 7-chloro-4-hydroxy-2-(2'-thienyl)quinazoline (6 g, 23 mmol), and dimethylamine in THF (2M, 50 mL) was heated at 220° C. in a steel bomb for 15 h. The reaction mixture was concentrated, washed with water, and chromatographed (SiO$_2$, 50% EtOAc in hexanes) to give 21% (1.3 g) of the title compound; m.p. 247–250° C.

Example 44

4-Chloro-7-Dimethylamino-2-(2'-Thienyl)Quinazoline

The title compound was prepared from 7-dimethylamino-4-hydroxy-2-(2'-thienyl)quinazoline (0.7 g, 2.6 mmol) as described in Example 3 to provide the desired compound in a 28% (0.21 g) yield; GC/MS calcd for C$_{14}$H$_{12}$ClN$_3$S (M+) 290, found 255 (M-Cl).

Example 45

4-(N-Aminocitraconamido)-7-Dimethylamino-2-(2'-Thienyl)Quinazoline

The title compound was prepared from 4-chloro-7-dimethylamino-2-(2'-thienyl)quinazoline (0.75 g, 2.6 mmol) as described in Example 4 to provide the desired compound in a 74% (0.49 g) yield; m.p. 199–200° C.

Example 46

2-(2'-Thienyl)-4H-3,1-Pyridoxazin-4-One

The title compound was prepared from 3-aminopyrionine-4-carboxylic acid (1 g, 7.2 mmol), as described in Example 1 to provide the desired compound in a 70% (1.4 g) yield; m.p. 119–120° C.

Example 47

4-HYDROXY-2-(2'-THIENYL)PYRIDOPYRIMIDINE

The title compound was prepared from 2-(2'-thienyl)-4H-3,1-pyridoxazin-4-one (0.83 g, 3.6 mmol) as described in Example 2 to provide the desired compound in a 73% (0.61 g) yield; m.p. 256–257° C.

Example 48

4-CHLORO-2-(2'-THIENYL)PYRIDOPYRIMIDINE

The title compound was prepared from 4-hydroxy-2-(2'-thienyl)pyridopyrimidine (0.47 g, 2.1 mmol) as described in Example 3 to provide the desired compound in a 91% (0.46 g) yield; m.p. 112–113° C.

Example 49

4-(N-AMINOCITRACONAMIDO)-2-(2'-THIENYL)PYRIDOPYRIMIDINE

The title compound was prepared from 4-chloro-2-(2'-thienyl)pyridopyrimidine (0.45 g, 1.8 mmol) as described in Example 4 to provide the desired compound in a 25% (0.15 g) yield; m.p. >253° C. (decomposed).

Example 50

4-HYDROXY-2-PHENYLQUNINAZOLINE

The title compound was prepared from 2-phenyl-4H-3,1-benzoxazin-4-one (2.0 g, 8.9 mmol) as described in Example 2 to provide the desired compound in a 94% (1.9 g) yield; m.p. 207–208° C.

Example 51

4-CHLORO-2-PHENYLQUNINAZOLINE

The title compound was prepared from 4-hydroxy-2-phenylquinazoline (0.5 g, 2.3 mmol) as described in Example 3 to provide the desired compound in a 83% (0.46 g) yield; m.p. 110–111° C.

Example 52

4-(N-AMINOCITRACONAMIDO)-2-PHENYLQUINAZOLINE

The title compound was prepared from 4-chloro-2-phenylquinazoline (0.44 g, 1.8 mmol) as described in Example 4 to provide the desired compound in a 61% (0.36 g) yield; m.p. 145–146° C.

Example 53

5-METHOXY-2-TRIFLUOROMETHYL-4H-3,1-BENZOXAZIN-4-ONE

A solution of 2-amino-6-methoxy benzoic acid (1.6 g, 9.6 mmol), trifluoroacetic anhydride (6.0 g, 29 mmol), and pyridine (2.3 g, 29 mmol) was stirred at room temperature for 0.5 h. The reaction mixture was diluted with EtOAc, washed with 1N HCl, saturated sodium bicarbonate, and brine. The organic layer was dried ($Na_2SO_4$), filtered and concentrated to give the title compound (1.5 g, 62%); m.p. 88–91° C.

Example 54

4-HYDROXY-5-METHOXY-2-TRIFLUOROMETHYLQUINAZOLINE

The title compound was prepared from 5-methoxy-2-trifluoromethyl-4H-3,1-benzoxazin-4-one (1.4 g, 5.7 mmol) as described in Example 2 to provide the desired compound in a 64% (0.89 g) yield; m.p. 249–250° C.

Example 55

4-CHLORO-5-METHOXY-2-TRIFLUOROMETHYLQUNINAZOLINE

The title compound was prepared from 4-hydroxy-5-methoxy-2-trifluoromethylquinazoline (0.8 g, 3.3 mmol) as described in Example 3 to provide the desired compound in a 70% (0.6 g) yield; m.p. 145–146° C.

Example 56

4-(N-AMINOCITRACONAMIDO)-5-METHOXY-2-TRIFLUOROMETHYLQUNINAZOLINE

The title compound was prepared from 4-chloro-5-methoxy-2-trifluoromethylquinazoline (0.4 g, 1.5 mmol) as described in Example 4 to provide the desired compound in a 56% (0.23 g) yield; m.p. 227–228° C.

Example 57

5-METHYL-2-TRIFLUOROMETHYL-4H-3,1-BENZOXAZIN-4-ONE

The title compound was prepared from 2-amino-6-methyl benzoic acid (3 g, 20 mmol) as described in Example 53 to provide the desired compound in a 89% (4 g) yield; m.p. 72–73° C.

Example 58

4-HYDROXY-5-METHYL-2-TRIFLUOROMETHYLQUNINAZOLINE

The title compound was prepared from 5-methyl-2-trifluoromethyl-4H-3,1-benzoxazin-4-one (3.0 g, 13 mmol) as described in Example 2 to provide the desired compound in a 64% (1.9 g) yield; m.p. 220–221° C.

Example 59

4-CHLORO-5-METHYL-2-TRIFLUOROMETHYLQUINAZOLINE

The title compound was prepared from 4-hydroxy-5-methyl -2-trifluoromethylquinazoline (1.8 g, 7.9 mmol) as described in Example 3 to provide the desired compound in a 62% (1.2 g) yield; m.p. 135–137° C.

Example 60

4-(N-AMINOCITRACONAMIDO)-5-METHYL-2-TRIFLUOROMETHYLQUINAZOLINE

The title compound was prepared from 4-chloro-5-methyl-2-trifluoromethylquinazoline (0.7 g, 2.8 mmol) as described in Example 4 to provide the desired compound in a 64% (0.32 g) yield; m.p. 169–170° C.

Example 61

7-CHLORO-2-TRIFLUOROMETHYL-4H-3,1-BENZOXAZIN-4-ONE

The title compound was prepared from 2-amino-4-chlorobenzoic acid (10 g, 58 mmol) as described in Example 53 to provide the desired compound in a 83% (12 g) yield; m.p. 46–48° C.

Example 62

7-Chloro-4-Hydroxy-2-Trifluoromethylquninazoline

The title compound was prepared from 7-chloro-2-trifluoromethyl-4H-3,1-benzoxazin-4-one (12 g, 48 mmol) as described in Example 2 to provide the desired compound in a 50% (6 g) yield; m.p. 168–170° C.

Example 63

4,7-Dichloro-2-Trifluoromethylquninazoline

The title compound was prepared from 7-chloro-4-hydroxy-2-trifluoromethylquinazoline (1 g, 4 mmol) as described in Example 3 to provide the desired compound in a 57% (0.61 g) yield; m.p. 46–47° C.

Example 64

4-(N-Aminocitraconamido)-7-Chloro-2-Trifluoromethylquinazoline

The title compound was prepared from 4,7-dichloro-2-trifluoromethylquinazoline (0.47 g, 1.8 mmol) as described in Example 4 to provide the desired compound in a 46% (0.29 g) yield; m.p. 224–225° C.

Example 65

7-(N-Piperidyl)-4-Hydroxy-2-(Trifluoromethyl)Quninazoline

The title compound was prepared from 7-chloro-4-hydroxy-2-trifluoromethylquinazoline (2.0 g, 8.0 mmol), as described in Example 43 (but using piperidine in place of N,N-dimethylamine) to provide the desired compound in a 96% (2.5 g) yield; m.p. 268–271° C.

Example 66

4-Chloro-7-(N-Piperidyl)-2-Trifluoromethylquinazoline

The title compound was prepared from 4-hydroxy-7-piperidyl-2-trifluoromethylquinazoline (0.75 g, 2.5 mmol) as described in Example 3 to provide the desired compound in a 92% (0.7 g) yield; m.p. 150–151° C.

Example 67

4-(N-Aminocitraconamido)-7-(N-Piperidyl)-2-Trifluoromethylquninazoline

The title compound was prepared from 4-chloro-7-(N-piperidyl)-2-trifluoromethylquinazoline (0.7 g, 2.2 mmol) as described in Example 4 to provide the desired compound in a 33% (0.3 g) yield; m.p. 124–126° C.

Example 68

6-Methylthio-2-Trifluoromethyl-4H-3,1-Benzoxazin-4-One

The title compound was prepared from 2-amino-5-methylthiobenzoic acid (4 g, 22 mmol) as described in Example 53 to provide the desired compound in a 39% (2.2 g); m.p. 93–95° C.

Example 69

4-Hydroxy-6-Methylthio-2-Trifluoromethylquinazoline

The title compound was prepared from 6-methylthio-2-trifluoromethyl-4H-3,1-benzoxazin-4-one (2.2 g, 8.4 mmol) as described in Example 2 to provide the desired compound in a 65% (1.2 g) yield; m.p. 244–245° C.

Example 70

4-Chloro-6-Mehylthio-2-Trifluoromethylquinazoline

The title compound was prepared from 4-hydroxy-6-methylthio-2-trifluoromethylquinazoline (1.8 g, 6.9 mmol) as described in Example 3 to provide the desired compound in a 65% (1.2 g) yield; m.p. 95–97° C.

Example 71

4-(N-Aminocitraconamido)-6-Methylthio-2-Trifluoromethylquninazoline

The title compound was prepared from 4-chloro-6-methylthio-2-trifluoromethylquinazoline (0.3 g, 1.1 mmol), as described in Example 4 to provide the desired compound in a 37% (0.15 g) yield; m.p. 226–228° C.

Example 72

4-Chloro-6-Methylsulfinyl-2-Trifluoromethylquninazoline

A solution of 4-chloro-6-methylthio-2-trifluoromethylquinazoline (0.4 g, 1.4 mmol) and m-chloroperbenzoic acid (0.3 g, 1.4 mmol) in chloroform (14 mL) was stirred at 0° C. for 0.5 h. The reaction mixture was washed with saturated sodium bisulfite solution, 1M sodium bicarbonate solution, and brine. The solution was dried ($Na_2SO_4$), filtered, and concentrated to give the title compound (0.2 g, 49%); m.p. 105–107° C.

Example 73

4-(N-Aminocitraconamido)-6-Methylsulfinyl-2-Trifluoromethylquninazoline

The title compound was prepared from 4-chloro-6-methylsulfinyl-2-trifluoromethylquinazoline (0.2 g, 0.68 mmol) as described in the Example 4 to provide the desired compound in a 59% (0.041 g) yield; m.p. 247–248° C.

Example 74

4-Chloro-6-Methylsulfonyl-2-Trifluoromethylquninazoline

The title compound was prepared from 4-chloro-6-methylthio-2-trifluoromethylquinazoline (0.35 g, 1.3 mmol) as described in Example 72 to provide the title compound (0.3 g, 90%); m.p. 184–186° C.

Example 75

4-(N-Aminocitraconamido)-6-METHYLSULFONYL-2-Trifluoromethylquninazoline

The title compound was prepared from 4-chloro-6-methylsulfonyl-2-trifluoromethylquinazoline (0.2 g, 0.65 mmol) as described in Example 4 to provide the desired compound in a 31% (0.075 g) yield; m.p. 258–260° C.

Example 76

2-Trifluoromethyl-4H-3,1-Benzoxazin-4-One

The title compound was prepared from anthranilic acid (1 g, 7.3 mmol), as described in Example 53 to provide the desired compound in a 99% (1.6 g) yield; m.p. 35–37° C.

Example 77

4-HYDROXY-2-TRIFLUOROMETHYLQUINAZOLINE

The title compound was prepared from 2-trifluoromethyl-4H-3,1-benzoxazin-4-one (1.5 g, 6.7 mmol) as described in Example 2 to provide the desired compound in a 76% (1.1 g) yield; m.p. 228–230° C.

Example 78

4-CHLORO-2-TRIFLUOROMETHYLQUNINAZOLINE

The title compound was prepared from 4-hydroxy-2-trifluoromethylquinazoline (1.0 g, 4.7 mmol) as described in Example 3 to provide the desired compound in a 88% (0.95 g) yield; m.p. 50–51° C.

Example 79

4-(N-AMINOCITRACONAMIDO)-2-TRIFLUOROMETHYLQUINAZOLINE

The title compound was prepared from 4-chloro-2-trifluoromethylquinazoline (0.9 g, 3.9 mmol) as described in Example 4 to provide the desired compound in a 81% (0.74 g) yield; m.p. 202–203° C.

Example 80

4-(AMINO-N-ISOCITRACONAMIDIC ACID)-2-TRIFLUOROMETHYLQUINAZOLINE

A solution of 4-hydrazino-2-trifluoromethylquinazoline (1.0 g, 4.4 mmol) and citraconic anhydride (0.5 g. 4.9 mmol) in dichloromethane (35 mL) was stirred at −78° C. for 16 hrs. The white precipitate was filtered and dried to give the title compound (1.4 g, 93%); m.p. 129–130° C.

Example 81

4-(AMINO-N-ISOCITRACONAMIDIC ACID)-6-METHOXY-2-(2'-THIENYL)QUNINAZOLINE

The title compound was prepared from 4-hydrazino-6-methoxy-2-(2'-thienyl)quinazoline (0.8 g, 2.9 mnol) as described in Example 80 to provide the compound in a 97% yield (1 g); m.p. 137–139° C.

Example 82

INHIBITION OF THE ACTIVATION OF NFκB AND AP-1

A. NFkB ASSAY

Stable human Jurkat T-cells containing an NFκB binding site (from the MHC promoter) fused to a minimal SV-40 promoter driving luciferase expression were used in this experiment. Cells were split to $3 \times 10^5$ cells/mL every 2–3 days (cell concentration should not exceed $1 \times 10^6$ cells/mL to keep the cells proliferating in log phase). These cells were counted, resuspended in fresh medium containing 10% Serum-Plus at a density of $1 \times 10^6$ cells/mL and plated in 96 well round bottom plates (200 μL per well) 18 hours prior to starting the experiment.

Compounds of this invention, dissolved in dimethyl sulfoxide (3.3, 0.33 and 0.03 μg/mL), were then added to the 96 well plates containing the cells and the plates are incubated for 0.5 h at 37° C. Then 50 ng/mL of phorbol 12-myristate-13-acetate (PMA) and 1 μg/mL of phytohemagglutinin (PHA) was added to each well and the cells were incubated for an additional 5 h at 37° C. The plates were centrifuged at 2200 RPM for 3 minutes at room temperature and then the medium was removed. To each well was added 60 μL of cell lysis buffer and the plates were left at room temperature for 0.25 h. Then 40 μL of each cell extract was transferred to a black 96 well plate and 50 μL of luciferase substrate buffer was added. Luminescence was immediately measured using a Packard TopCount.

B. AP-1 ASSAY

For AP-1, the assay was run as described above for NFκB except stable Jurkat T-cells were used that contained a the −73 collagenase promoter driving luciferase expression. In addition, the concentration of PMA used was 5 ng/mL.

C. RESULTS

The results of the above assays (expressed as $IC_{50}$'s, μM) for representative compounds of this invention, as percent inhibition versus control, are presented in Table 3. β-actin was employed as a control cell line indicating effects on transcription. The lack of β-actin activity evidences selectivity of the test compounds for the transcription factors AP-1 and NFκB.

TABLE 3

| Cpd.No. | Example No. | AP-1 | NFkB |
|---|---|---|---|
| 1 | 52 | 0.2 | 0.1 |
| 2 | 49 | 0.1 | 0.1 |
| 3 | 79 | 0.1 | 0.01 |
| 4 | 56 | 0.01 | 0.01 |
| 5 | 60 | 0.5 | 0.2 |
| 6 | 64 | 0.3 | 0.1 |
| 7 | 67 | 0.3 | 0.1 |
| 8 | 71 | 0.09 | 0.06 |
| 10 | 75 | 10 | 8 |
| 11 | 4 | 0.07 | 0.04 |
| 12 | 5 | 1.7 | 2.2 |
| 13 | 9 | 0.008 | 0.008 |
| 14 | 14 | 0.003 | 0.002 |
| 15 | 18 | 0.02 | 0.01 |
| 16 | 22 | 0.02 | 0.02 |
| 17 | 26 | 0.07 | 0.04 |
| 18 | 30 | 0.02 | 0.01 |
| 19 | 10 | 0.07 | 0.1 |
| 20 | 33 | 0.07 | 0.2 |
| 21 | 36 | 0.03 | 0.02 |
| 22 | 40 | 0.03 | 0.01 |
| 23 | 45 | 0.04 | 0.04 |

Based on the results of this experiment, representative compounds of this invention were found to be effective at inhibiting the activation of transcription factors (i.e., NFκB and 1) involved in gene transcription, and therefore have utility as, for example, immunosuppressive agents.

Example 83

INHIBITION OF CYTOKINES

To determine the effects of compounds on PMA/PHA-induced cytokine production, supernatants from either the NFκB (for IL-8) and AP-1 (for IL-2) reporter gene assays of Example 82 were collected and saved. Cytokine levels in the supernatants (25–50 μL aliquots) were determined by ELISA. The results of this experiment for repesentative compounds of this invention are presented in Table 4 (expressed as percent inhibition versus control).

TABLE 4

| Cpd.No. | Example No. | IC$_{50}$ ($\mu$M) IL-2 | IL-8 |
|---|---|---|---|
| 1 | 52 | 0.01 | 0.002 |
| 2 | 49 | 0.7 | 0.1 |
| 3 | 79 | 0.05 | 0.03 |
| 4 | 56 | 0.12 | 0.05 |
| 5 | 60 | 0.02 | 0.002 |
| 6 | 64 | 0.5 | 0.05 |
| 7 | 67 | 0.07 | 0.005 |
| 8 | 71 | 0.04 | 0.05 |
| 12 | 9 | 0.009 | 0.01 |
| 13 | 14 | 0.0008 | 0.0005 |
| 14 | 18 | 0.01 | 0.004 |
| 15 | 22 | 0.2 | 0.05 |
| 16 | 26 | 0.2 | 0.1 |
| 17 | 30 | 0.04 | 0.01 |
| 18 | 10 | 0.1 | 0.2 |
| 19 | 33 | 0.4 | 0.1 |
| 20 | 36 | 0.2 | 0.008 |
| 21 | 40 | 0.3 | 0.2 |
| 22 | 45 | 0.02 | 0.01 |

Example 84

IN VIVO ACTIVITY

The murine popliteal lymph node (PLN) assay is a graft vs. host model that predicts activity of compounds in blocking human transplant rejection. The delayed-type hypersensitivity response to oxazolone is a standard contact sensitivity model. Both of these models are used routinely to evaluate compounds that are used clinically. For example, cyclosporin and cyclophosphamide are active in these models and are used clinically (Morris et al., *Transplantation Proceedings* 22(Suppl. 1):110–112, 1990). Thus, the compounds of this invention may be assayed according to the following procedures.

A. POPLITEAL LYMPH NODE MODEL

Spleens removed from donor BALB/c mice and splenocytes are isolated then irradiated (3,000 rads) to prevent donor cell proliferation. After washing and adjusting cell density, 2.5×10$^6$ cells are injected subcutaneously into the left hind footpad of C3H mice. On day 4, the mice are sacrificed and left popliteal lymph nodes (PLNs) weighed.

A compound of this invention is administered once daily by intraperitoneal injection beginning one day before footpad injection (day 0) through day 4. The compound is suspended, immediately prior to use, at a concentration of 5 mg/mL in 0.25% methyl cellulose (Sigma) using a glass-Teflon homogenizer. For doses of 10, 20 and 30 mg/kg, appropriate dilutions of the stock solution are made so that 0.1 mL/10 g body weight is administered by intraperitoneal injection.

B. DELAYED TYPE HYPERSENSITIVITY STUDY

On day 0, oxazolone (100 $\mu$L of a 3% solution) is applied to the shaved abdomen of mice. On day 7, a challenge application of oxazolone was applied (10 $\mu$L) around the right ear. A compound of this invention is administered from days -2 to 7 by intraperitoneal injection. It is prepared immediately prior to use by suspending it in 0.25% methyl cellulose (Sigma) using a glass-teflon homogenizer. For each dose, 0.1 mL/10 g body weight of the suspension is administered. The compound is prepared at the highest concentration for that study and appropriate dilutions of the stock solution are made so that 0.1 mL/10 g body weight was administered. Twenty four hours later, the difference in right vs. left ear thickness is measured.

It will be appreciated that, although specific embodiments of this invention have been described herein for purpose of illustration, various modifications may be made without departing from the spirit and scope of the invention.

We claim:

1. A compound having the structure:

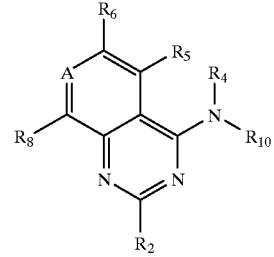

wherein

R$_{10}$ is selected from the following structures:

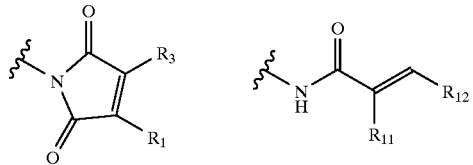

A is C(R$_7$);

R$_1$ and R$_3$ are independently selected from hydrogen or an unsubstituted or substituted C$_{1-8}$alkyl or C$_{6-12}$aryl;

R$_2$ is selected from an unsubstituted or substituted C$_{1-8}$alkyl, C$_{6-12}$aryl, C$_{7-12}$aralkyl, C$_{3-12}$heterocycle or C$_{4-16}$heterocyclealkyl;

R$_4$ is selected from hydrogen or an unsubstituted C$_{1-8}$alkyl;

R$_5$, R$_6$, R$_7$ and R$_8$ are independently selected from hydrogen, —NO$_2$, —CN, halogen, C$_{1-8}$alkyl, X-C$_{1-8}$alkyl, C$_{3-12}$heterocycle or —COOR$_9$, where X is selected from —O—, —S—, —S(=O)—, —S(=O)$_2$—, —NH— or —N(C$_{1-8}$alkyl)-, and R$_9$ is selected from hydrogen or an unsubstituted or substituted C$_{1-8}$alkyl, C$_{6-12}$aryl or C$_{7-12}$aralkyl;

R$_{11}$ is selected from hydrogen or an unsubstituted or substituted C$_{1-8}$alkyl or C$_{6-12}$aryl; and R$_{12}$ is selected from hydrogen, —COOR$_9$, —CONHR$_9$, or an unsubstituted or substituted C$_{1-8}$alkly or C$_{6-12}$aryl.

2. The compound of claim 1 having the structure:

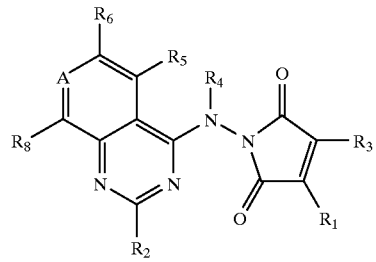

3. The compound of claim 1 having the structure:

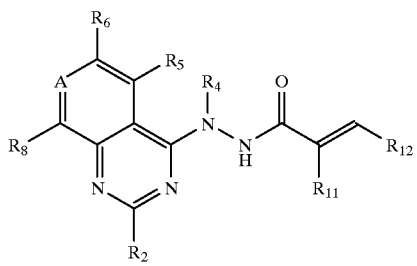

4. The compound of claim 2 wherein $R_1$ is methyl.
5. The compound of claim 2 wherein $R_2$ is selected from —$C_6H_5$, —$CF_3$ and 2'-thienyl.
6. The compound of claim 5 wherein $R_2$ is 2'-thienyl.
7. The compound of claim 2 wherein $R_3$ is hydrogen.
8. The compound of claim 2 wherein $R_4$ is hydrogen or methyl.
9. The compound of claim 8 wherein $R_4$ is hydrogen.
10. The compound of claim 2 wherein $R_5$ is selected from hydrogen, halogen, methoxy and methyl.
11. The compound of claim 10 wherein $R_5$ is methoxy.
12. The compound of claim 2 wherein $R_6$ is hydrogen.
13. The compound of claim 2 wherein $R_7$ is selected from hydrogen, halogen and methoxy.
14. The compound of claim 13 wherein $R_7$ is hydrogen.
15. The compound of claim 2 wherein $R_8$ is hydrogen.
16. The compound of claim 2 wherein A is $C(R_7)$.
17. A composition comprising a compound of claim 1 and a pharmaceutically acceptable carrier or diluent.
18. A method for treating an inflammatory condition, comprising administering to a warm-blooded animal in need thereof an effective amount of a compound of claim 1.
19. The method of claim 18 wherein the inflammatory condition is an immunoinflammatory condition.
20. The method of claim 19 wherein the immunoinflammatory condition is selected from rheumatoid arthritis, osteoarthritis, transplant rejection, sepsis, ARDS and asthma.
21. The method of claim 19 wherein the immunoinflammatory condition is rheumatoid arthritis.
22. The method of claim 18 wherein the inflamnmatory condition is an autoimmune disease.
23. The method of claim 22 wherein the autoimmune disease is selected from multiple sclerosis, psoriasis, inflammatory bowel disease, glomerulonephritis, lupus, uveitis and chronic hepatitis.
24. The method of claim 18 wherein the inflammatory condition is selected from trauma, oxidative stress, cell death, irradiation damage, ischemia, reperfusion, cancer and viral infection.
25. The method of claim 18 wherein the inflammatory condition is transplant rejection.

* * * * *